(12) United States Patent
Hasegawa et al.

(10) Patent No.: US 12,318,168 B2
(45) Date of Patent: Jun. 3, 2025

(54) IN VIVO PRESSURE MEASUREMENT DEVICE

(71) Applicant: FURUKAWA ELECTRIC CO., LTD., Tokyo (JP)

(72) Inventors: Hideaki Hasegawa, Tokyo (JP); Hiroyuki Tamaoka, Tokyo (JP); Takashi Fujihata, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 148 days.

(21) Appl. No.: 18/178,666

(22) Filed: Mar. 6, 2023

(65) Prior Publication Data

US 2023/0200658 A1 Jun. 29, 2023

Related U.S. Application Data

(63) Continuation of application No. PCT/JP2021/034182, filed on Sep. 16, 2021.

(30) Foreign Application Priority Data

Sep. 16, 2020 (JP) .................................. 2020-155186

(51) Int. Cl.
*A61B 5/00* (2006.01)
*A61B 5/0215* (2006.01)

(52) U.S. Cl.
CPC .......... *A61B 5/0084* (2013.01); *A61B 5/0215* (2013.01); *A61B 2562/0285* (2013.01)

(58) Field of Classification Search
CPC ................ A61B 5/0084; A61B 5/0215; A61B 2562/0285
See application file for complete search history.

(56) References Cited

U.S. PATENT DOCUMENTS 4,915,473 A 4/1990 Haese et al.
5,357,804 A * 10/1994 Wesemann ................ G01L 1/02
250/231.19
(Continued)

FOREIGN PATENT DOCUMENTS

CN 102667551 A 9/2012
EP 3 940 354 A1 1/2022
(Continued)

OTHER PUBLICATIONS

Extended European Search Report issued Jul. 22, 2024 in European Patent Application No. 21869432, 16 pages.
(Continued)

*Primary Examiner* — Dixomara Vargas
(74) *Attorney, Agent, or Firm* — Oblon, McClelland, Maier & Neustadt, L.L.P.

(57) ABSTRACT

An in vivo pressure measurement device includes: a light source configured to output test light; an optical fiber, to which the test light is input, at least partially including a sensor optical fiber configured to transmit the test light with a loss of 0.3 dB/m or more; and a light receiving unit configured to receive the test light transmitted through the sensor optical fiber. The in vivo pressure measurement device is configured to measure pressure in a living body acting on the sensor optical fiber based on intensity of the test light received at the light receiving unit.

22 Claims, 7 Drawing Sheets

(56) References Cited

U.S. PATENT DOCUMENTS

| | | | |
|---|---|---|---|
| 5,929,989 A * | 7/1999 | Mori | G01L 11/02 356/477 |
| 6,677,576 B1 | 1/2004 | Kenny et al. | |
| 10,258,240 B1 * | 4/2019 | Eberle | A61B 5/0084 |
| 2004/0246489 A1 * | 12/2004 | Kinugasa | G01L 13/025 356/477 |
| 2008/0183059 A1 | 7/2008 | LaPlante et al. | |
| 2009/0024177 A1 * | 1/2009 | Shuros | A61B 5/0006 607/22 |
| 2012/0065482 A1 * | 3/2012 | Robinson | A61B 5/150389 600/309 |
| 2013/0317372 A1 | 11/2013 | Eberle et al. | |
| 2014/0350414 A1 | 11/2014 | Mcgowan et al. | |
| 2015/0077736 A1 * | 3/2015 | Reinsch | G01N 21/55 356/32 |
| 2015/0141842 A1 * | 5/2015 | Spanier | A61M 60/237 600/478 |
| 2015/0141843 A1 * | 5/2015 | Eberle | A61B 5/6851 600/478 |
| 2015/0141854 A1 * | 5/2015 | Eberle | A61B 5/02154 600/488 |
| 2016/0262627 A1 * | 9/2016 | Hecker | A61B 5/205 |
| 2018/0160947 A1 | 6/2018 | Hu | |
| 2018/0228385 A1 | 8/2018 | Eberle et al. | |
| 2018/0325393 A1 | 11/2018 | Shinohara et al. | |
| 2019/0159688 A1 | 5/2019 | De Groot et al. | |
| 2019/0217002 A1 * | 7/2019 | Urakabe | A61M 1/3639 |
| 2019/0357751 A1 * | 11/2019 | Friedlander | A61B 1/015 |
| 2020/0305999 A1 * | 10/2020 | Szoka | A61B 1/00066 |
| 2021/0169347 A1 | 6/2021 | Ito et al. | |
| 2022/0280298 A1 * | 9/2022 | Schwarcz | A61F 2/2433 |
| 2023/0191095 A1 * | 6/2023 | Chen | A61B 5/032 604/9 |

FOREIGN PATENT DOCUMENTS

| | | |
|---|---|---|
| JP | 2015-517678 A | 6/2015 |
| JP | 2016-525908 A | 9/2016 |
| JP | 2018-187146 A | 11/2018 |
| JP | 2018-532987 A | 11/2018 |
| JP | 2020-28478 A | 2/2020 |

OTHER PUBLICATIONS

International Search Report issued Oct. 26, 2021 in PCT/JP2021/034182 filed Sep. 16, 2021, 2 pages.

Office Action issued Mar. 22, 2025, in corresponding Chinese Patent Application No. 202180054615.0 with English translation, citing documents 1 and 15 therein 24 pages.

* cited by examiner

IN VIVO PRESSURE MEASUREMENT DEVICE

This application is a continuation of International Application No. PCT/JP2021/034182, filed on Sep. 16, 2021 which claims the benefit of priority of the prior Japanese Patent Application No. 2020-155186, filed on Sep. 16, 2020, the entire contents of which are incorporated herein by reference.

BACKGROUND

The present disclosure relates to an in vivo pressure measurement device.

Background

An invasive blood pressure monitor as disclosed in Japanese Patent Application Laid-open No. 2018-187146 and a non-invasive blood pressure monitor as disclosed in Japanese Patent Application Laid-open No. 2020-028478 are known.

SUMMARY

In both types of blood pressure monitors, it would be beneficial if the size thereof may be made smaller and the structure thereof may be more simplified, for example.

In addition to blood pressure, it would be even more beneficial if pressure and forces acting in a living body may be measured as well.

There is a need for a more improved and new in vivo pressure measurement device.

According to one aspect of the present disclosure, there is provided an in vivo pressure measurement device including: a light source configured to output test light; an optical fiber, to which the test light is input, at least partially including a sensor optical fiber configured to transmit the test light with a loss of 0.3 dB/m or more; and a light receiving unit configured to receive the test light transmitted through the sensor optical fiber, wherein the in vivo pressure measurement device is configured to measure pressure in a living body acting on the sensor optical fiber based on intensity of the test light received at the light receiving unit.

According to another aspect of the present disclosure, there is provided an in vivo pressure measurement device including: a light source configured to output test light; an optical fiber, to which the test light is input, including a sensor part from which light leaks due to an applied external force; and a light receiving unit configured to receive the test light transmitted through the sensor part, wherein the in vivo pressure measurement device is configured to measure pressure in a living body acting on the sensor part based on intensity of the test light received at the light receiving unit.

DETAILED DESCRIPTION

Hereinafter, exemplary embodiments and modifications of the present disclosure will be disclosed. The configurations of the embodiments and modifications presented below as well as the actions and results (effects) brought about by such configurations are examples. The present disclosure may also be achieved by configurations other than those disclosed in the following embodiments and modifications. In addition, according to the present disclosure, it is possible to acquire at least one of the various kinds of effects (including derivative effects) achieved by the configurations.

The embodiments and modifications described hereinafter have similar constituent elements. Therefore, according to the configuration of each of the embodiments and modifications, it is possible to acquire similar actions and effects based on the similar constituent elements. Furthermore, hereinafter, similar reference signs may be applied to the similar constituent elements, and duplicated explanations may be omitted.

In the present descriptions, ordinal numbers are assigned for convenience in order to distinguish components, members, parts, and the like, and do not indicate priority or order thereof.

Figure 1:
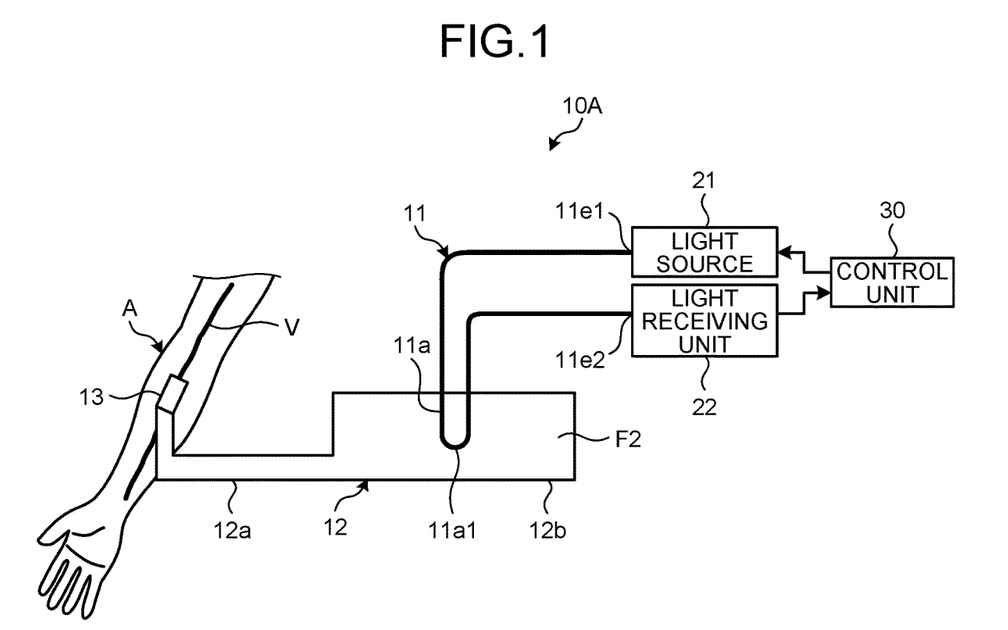
FIG. 1 is an exemplary schematic diagram of an in vivo pressure measurement device according to a first embodiment.

FIG. 1 is a schematic diagram of a pressure measurement device 10A according to a first embodiment. In the present embodiment, the pressure measurement device 10A is a device that measures blood pressure as fluid pressure in a living body, which is an invasive blood pressure measurement device. Note that blood is an example of a fluid in a living body A as a target of pressure measurement, and may also be referred to as a first fluid. The pressure measurement device 10A is an example of an in vivo pressure measurement device.

As illustrated in FIG. 1, the pressure measurement device 10A includes an optical fiber 11, a tube set 12, a catheter 13, a light source 21, a light receiving unit 22, and a control unit 30.

An end part 11e1 in the longitudinal direction of the optical fiber 11 is optically connected to the light source 21, and an end part 11e2 in the longitudinal direction of the optical fiber 11 is optically connected to the light receiving unit 22. Test light emitted from the light source 21 is input into the optical fiber 11 from the end part 11e1, transmitted through the optical fiber 11 including a sensor part 11a, output outside the optical fiber 11 from the end part 11e2, and received at the light receiving unit 22. The end part 11e1 is an example of one end, and the end part 11e2 is an example of the other end.

The light source 21 has, for example, a laser diode that outputs light with a wavelength of 400 [nm] or more and 500 [nm] or less, for example. The light source 21 may also output optical pulses intermittently at prescribed time intervals.

The light receiving unit 22 has, for example, a photodiode, and detects intensity of light input from the optical fiber 11, that is, intensity of the light passing through the sensor part 11a. The light receiving unit 22 may also be referred to as a detection unit.

The control unit 30 may acquire the intensity of the light received at the light receiving unit 22. In addition, the control unit 30 may switch emission and non-emission of test light at the light source 21 and change the output state of the test light.

The catheter 13 is placed on the surface of the living body A, and its tip (not illustrated) is inserted into a blood vessel V.

The inside of the tube set 12 is filled with a fluid different from blood, such as a saline solution F2, for example. The catheter 13 and the tube set 12 are configured such that the blood pressure inside the blood vessel V is propagated to the saline solution F2. The saline solution F2 is an example of an ex vivo fluid, which may also be referred to as a second fluid.

The tube set 12 includes a tube 12a and a chamber 12b expanded from the tube 12a. The chamber 12b has the sensor part 11a of the optical fiber 11 inserted thereto. As is apparent from FIG. 1, the tube set 12 is located outside the living body A. Therefore, in the present embodiment, the sensor part 11a is located outside the living body A. The sensor part 11a detects the pressure of the saline solution F2 to which the pressure of blood is propagated. Note that the tube set 12 may not have the chamber 12b, and the sensor part 11a may be inserted into the tube 12a.

Figure 2:
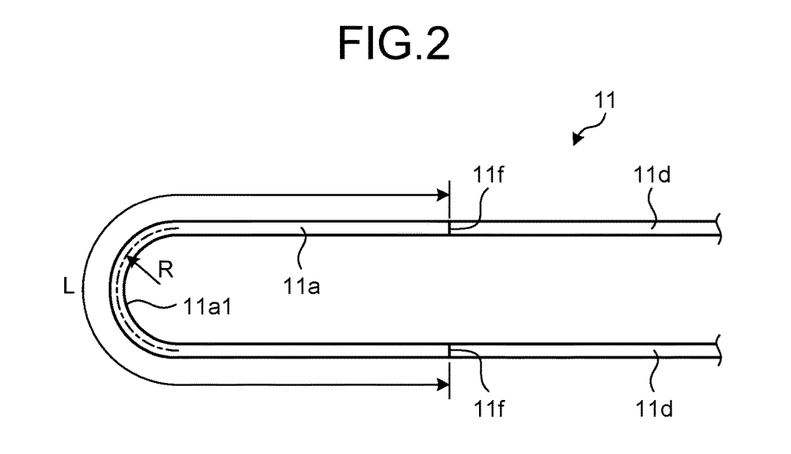
FIG. 2 is an exemplary schematic diagram of an optical fiber according to the embodiment.

FIG. 2 is a schematic diagram of the optical fiber 11. As illustrated in FIG. 2, the optical fiber 11 includes the sensor part 11a and two delivery optical fibers 11d. The sensor part 11a is an optical fiber interposed between the two delivery optical fibers 11d. In other words, one delivery optical fiber 11d, the sensor part 11a that is an optical fiber, and the other delivery optical fiber 11d are mechanically and optically connected in series. The transmission loss of the delivery optical fiber 11d is lower than the transmission loss of the sensor part 11a. The effective relative refractive-index difference of the delivery optical fiber 11d is larger than the effective relative refractive-index difference of the sensor part 11a. Furthermore, at a boundary 11f between the sensor part 11a and the delivery optical fiber 11d, the sensor part 11a and the delivery optical fiber 11d are fusion-spliced. The sensor part 11a is an example of a sensor optical fiber.

Figure 3:
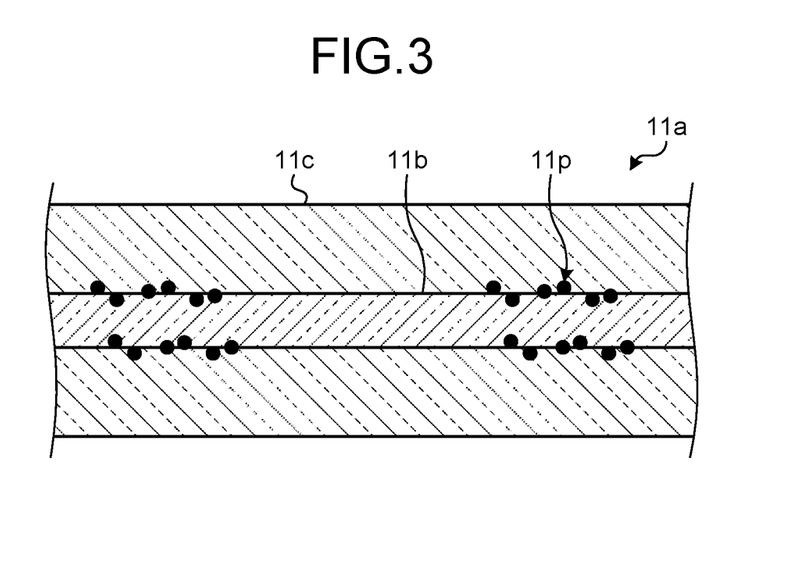
FIG. 3 is an exemplary and schematic cross-sectional view taken along the longitudinal direction of a part of a sensor part according to the embodiment.
Figure 4:
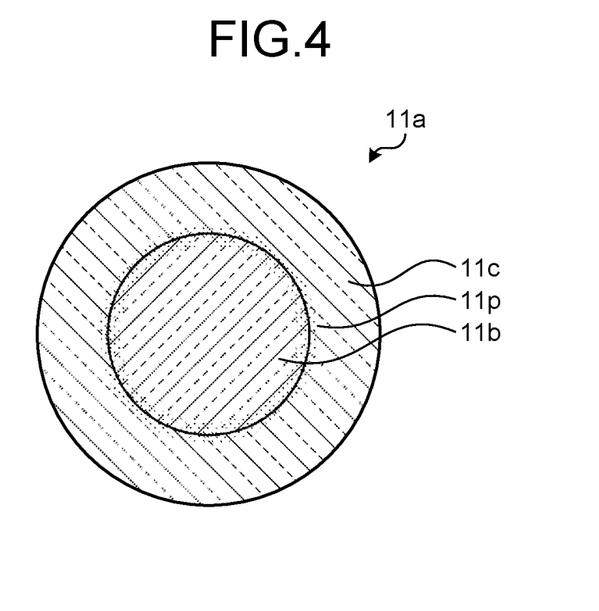
FIG. 4 is an exemplary and schematic cross-sectional view perpendicular to the longitudinal direction of the sensor part according to the embodiment.

FIG. 3 is a cross-sectional view of a part of the sensor part 11a along the longitudinal direction, and FIG. 4 is a cross-sectional view of the sensor part 11a perpendicular to the longitudinal direction.

As is apparent from FIGS. 3 and 4, the sensor part 11a includes a core 11b and a cladding 11c that surrounds the core 11b and has a lower refractive index than that of the core 11b.

The diameter of the core 11b and the relative refractive-index difference of the core 11b with respect to the cladding 11c are set such that the sensor part 11a may transmit test light in a single mode. Furthermore, the cladding 11c may be surrounded by a coating (not illustrated). The coating in this case exhibits transparency to the test light.

Furthermore, as an example, the diameter of the cladding, that is, the outer diameter of the core wire, is the same for the sensor part 11a and the delivery optical fiber 11d. The diameter (outer diameter) of the core may also be the same or different for the sensor part 11a and the delivery optical fiber 11d. As an example, the diameter of the core of the delivery optical fiber 11d may be larger than the diameter of the core 11b of the sensor part 11a. Furthermore, the delivery optical fiber 11d may be a multi-mode optical fiber that transmits the test light in a multi-mode.

The sensor part 11a and the delivery optical fiber 11d are what is called plastic fibers made of a synthetic resin material transparent to the test light, such as methacrylic resin or fluororesin. However, not limited to this, the sensor part 11a and the delivery optical fiber 11d may be glass optical fibers made of a quartz glass material. The sensor part 11a and the delivery optical fiber 11d may also be made of materials different from each other.

Furthermore, as illustrated in FIGS. 3 and 4, the sensor part 11a may include a plurality of nanostructures 11p near the interface between the core 11b and the cladding 11c. However, distribution of such nanostructures 11p is an example, and the nanostructures 11p may exist throughout the entire radial direction of the cladding 11c within the sensor part 11a. Each of the nanostructures 11p may contain fillers (for example, particles such as fine particles or cylindrical tubes) and voids (for example, microscopic spaces of air other than tubes or fine particles), and may contain at least two kinds of those examples. The nanostructure 11p, for example, has a cross-sectional diameter of 100 [nm] or less in the cross section perpendicular to the longitudinal direction of the sensor part 11a. In this case, the loss in the sensor part 11a tends to increase compared to the case without fillers and voids. Fillers and voids may be contained more in the cladding 11c than in the core 11b of the sensor part 11a.

Through the intensive sturdies of the inventors, it is found that in the sensor part 11a with such a configuration, the test light is scattered by the nanostructures 11p, which makes it more difficult for the test light to be confined in the core 11b than in a configuration without the nanostructures 11p, that is, the test light tends to leak from the core 11b. In this case, it is also found that the greater the external force acting on the sensor part 11a, the greater the leakage of the test light from the sensor part 11a, that is, the greater the transmission loss in the sensor part 11a. Furthermore, for such a sensor part 11a where the test light tends to leak from the core 11b, it is also found that, when an external force is applied, the transmission loss changes more sensitively in response to the external force. As an example, it is found that such characteristics become more prominent when the transmission loss for the test light at the sensor part 11a is 0.3 [dB/m] or more. This is because light leaks to the outside of the cladding 11c when the transmission loss is 0.3 [dB/m] or more, and light sensitively reacts to changes in the nanostructures 11p near the cladding 11c caused due to the external pressure, which significantly affects the transmission loss.

From these characteristics of the sensor part 11a, the control unit 30 may calculate the pressure of the saline solution F2 at the sensor part 11a corresponding to the intensity of light received at the light receiving unit 22, and thus the pressure of blood, that is, the blood pressure, based on a correlation between the intensity of light received at the light receiving unit 22 acquired in advance experimentally and the pressure acted on the sensor part 11a. The control unit 30 is an example of an arithmetic processing unit.

Furthermore, as illustrated in FIG. 2, the sensor part 11a has a curved part 11a1 folded in a U-like shape. The curved part 11a1 may also be referred to as a bent part or a folded part. Through the intensive studies of the inventors, for the sensor part 11a, it is found that a length L of the sensor part 11a is preferable to be between 1 [cm] and 4 [cm], both inclusive, and a curvature radius R of the curved part 11a1 (radius of the central axis of the sensor part 11a) to be between 50 [μm] and 200 [μm], both inclusive.

Figure 5:
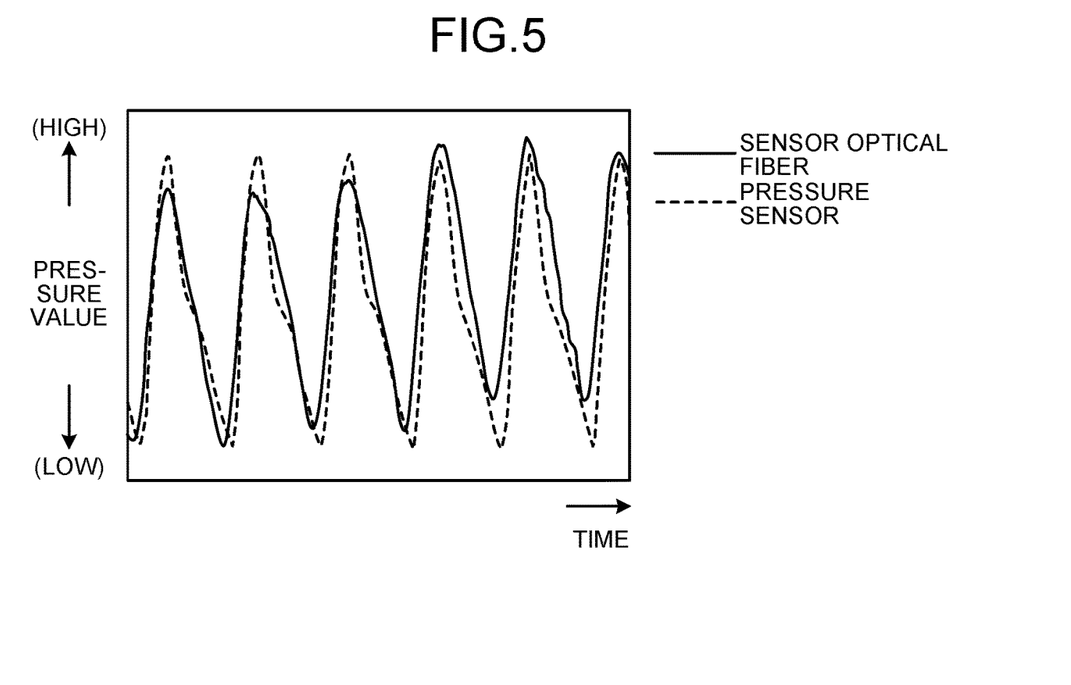
FIG. 5 is a graph presenting an example of change over time of detection values of pressure acquired by the in vivo pressure measurement device of the embodiment and a known pressure sensor.

FIG. 5 is a graph presenting an example of changes over time of detection values of pressure acquired by the pressure measurement device 10A of the present embodiment and a known pressure sensor. This graph indicates the measurement results of the pressure of a test fluid in an experimental facility that may schematically create pressure changes in the test fluid equivalent to changes in blood pressure caused by heart beats. From FIG. 5, it may be seen that the detection values of the pressure of the test fluid are in good agreement between the pressure measurement device 10A of the present embodiment indicated by a solid line and the known pressure sensor indicated by a dashed line. The inventors have experimentally confirmed that, according to the pressure measurement device 10A of the present embodiment, it is possible to acquire the measurement performance that is equal to or better than that of known pressure sensors, as in this example.

As described above, in the present embodiment, the light receiving unit 22 receives the test light emitted from the light source 21 and transmitted in the optical fiber 11 including the sensor part 11a (sensor optical fiber). The transmission loss of the test light at the sensor part 11a increases as the external force such as fluid pressure acting on the sensor part 11a increases. The control unit 30 measures the blood pressure (fluid pressure in a living body) acting on the sensor part 11a based on the optical intensity of the test light received at the light receiving unit 22.

With such a configuration, the pressure measurement device 10A may be achieved by a more compact and simpler configuration with optical fibers being the base.

In addition, as in the present embodiment, the sensor part 11a may be a plastic fiber.

With such a configuration, for example, the sensor part 11a may be configured more flexibly, so that the increment ratio of the transmission loss of the test light to the increment in the fluid pressure in the sensor part 11a, that is, the rate of increase, may be made larger. In other words, such a configuration may increase the detection sensitivity of the sensor part 11a for the fluid pressure.

Furthermore, as in the present embodiment, the sensor part 11a may be the optical fiber that transmits the test light with a loss of 0.3 [dB/m] or more.

As in the present embodiment, the sensor part 11a may also have the curved part 11a1.

In addition, as in the present embodiment, the sensor part 11a may include the plurality of nanostructures 11p.

Furthermore, in the present embodiment, the delivery optical fiber 11d between the sensor part 11a and the light source 21 is a multi-mode optical fiber, while the sensor part 11a may be a single-mode optical fiber.

With such a configuration, for example, the test light tends to leak more easily from the sensor part 11a, so that the detection sensitivity of the sensor part 11a for the fluid pressure may be increased.

Furthermore, as in the present embodiment, the light receiving unit 22 may also receive the test light that is input into the optical fiber 11 from the light source 21 via the end part 11e (one end) and output from the end part 11e2 (other end) via the sensor part 11a.

With such a configuration, the intensity of received light may be increased, and thus the measurement accuracy may be further improved, compared to a configuration in which the light receiving unit 22 receives light reflected at one end of the optical fiber 11, for example.

Furthermore, in the present embodiment, the sensor part 11a measures the pressure of the saline solution F2 (ex vivo fluid) to which the blood pressure (pressure of an in vivo fluid) is propagated.

The configuration of the present embodiment may be applied to an invasive blood pressure measurement device that indirectly measures the pressure of an in vivo fluid via an ex vivo fluid by the sensor part 11a located outside a living body.

Figure 6:
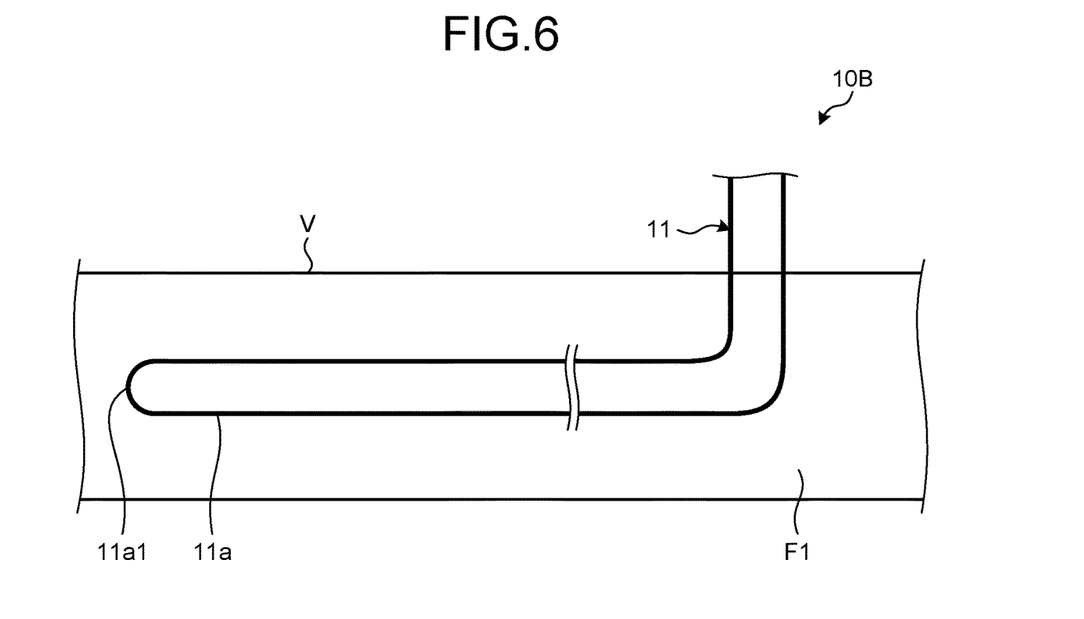
FIG. 6 is an exemplary schematic diagram of an in vivo pressure measurement device according to a second embodiment.

FIG. 6 is a schematic diagram of a part of a pressure measurement device 10B according to a second embodiment, which is a cross-sectional view along the longitudinal direction of an optical fiber 11 in a blood vessel V. The optical fiber 11 of the present embodiment is optically connected to a light source 21 and a light receiving unit 22, as in the first embodiment described above. In other words, in the present embodiment, test light input into the optical fiber 11 from the light source 21 is also transmitted in the optical fiber 11 including a sensor part 11a, and received at the light receiving unit 22. A control unit 30 calculates the pressure acted on the sensor part 11a based on the optical intensity of the test light received at the light receiving unit 22.

As illustrated in FIG. 6, in the present embodiment, the optical fiber 11 is inserted into the blood vessel V. With such a configuration, the higher the pressure of blood F1 that is a fluid in the blood vessel V, the greater the transmission loss of the test light at the sensor part 11a. The blood F1 is an example of an in vivo fluid, which may also be referred to as a first fluid.

Through the intensive studies of the inventors, for the sensor part 11a also in the pressure measurement device 10B of the present embodiment, it is found that a length L of the sensor part 11a (see FIG. 2) is preferable to be between 1 [cm] and 4 [cm], both inclusive, and a curvature radius R of a curved part 11a1 (radius of the central axis of the sensor part 11a, see FIG. 2) to be between 50 [μm] and 200 [μm], both inclusive. The area of such a curvature radius R is an area where the bending loss increases sensitively to the pressure, which further improves the sensor sensitivity to the pressure.

With the present embodiment, it is possible to acquire the effects similar to those of the first embodiment described above. The pressure measurement device 10B of the present embodiment may be applied to an invasive blood pressure measurement device that directly measures the pressure of an in vivo fluid by the sensor part 11a located inside a living body.

Figure 7:
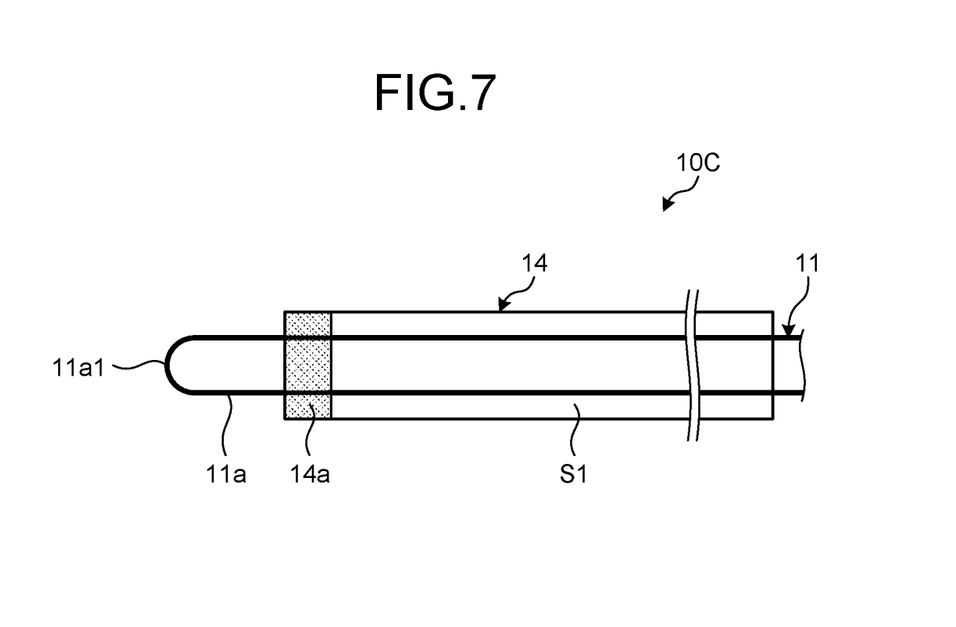
FIG. 7 is an exemplary schematic diagram of an in vivo pressure measurement device according to a third embodiment.

FIG. 7 is a schematic diagram of a part of a pressure measurement device 10C according to a third embodiment, which is a cross-sectional view along the longitudinal direction of an optical fiber 11. The optical fiber 11 of the present embodiment is optically connected to a light source 21 and a light receiving unit 22, as in the first embodiment described above. In other words, in the present embodiment, test light input into the optical fiber 11 from the light source 21 is also transmitted in the optical fiber 11 including a sensor part 11a, and received at the light receiving unit 22. A control unit 30 calculates the pressure acted on the sensor part 11a based on the optical intensity of the test light received at the light receiving unit 22. The sensor part 11a of the present embodiment is inserted into the blood vessel V, as in the second embodiment described above.

As illustrated in FIG. 7, in the present embodiment, the pressure measurement device 10C includes a tubular member 14 that surrounds the optical fiber 11. In other words, the tubular member 14 houses the optical fiber 11 inside the tube. The tubular member 14 surrounds both outward path and return path of the optical fiber 11 to/from the sensor part 11a, and the sensor part 11a is exposed from the tip of the tubular member 14. The tubular member 14 protects the optical fiber 11.

The optical fiber 11 penetrates through a fixing member 14a. The fixing member 14a positions the optical fiber 11 and the tubular member 14 in prescribed relative positions. In the present embodiment, the fixing member 14a, for example, fixes the optical fiber 11 and the tubular member 14 such that the optical fiber 11 is separated from the peripheral wall of the tubular member 14 at least at the position where the fixing member 14a is provided, and that the outward path and the return path of the optical fiber 11 are separated from each other. While the pressure measurement device 10C in the example of FIG. 7 has only one fixing member 14a, the pressure measurement device 10C is not limited thereto and may have a plurality of fixing members 14a disposed with a space provided therebetween along the longitudinal direction of the tubular member 14. The fixing member 14a is an adhesive, for example, but not limited thereto.

Furthermore, the tubular member 14 exhibits flexibility and elasticity. Thus, with such a configuration, by setting the specifications of the tubular member 14 appropriately, for example, the subassembly having the tubular member 14 and the optical fiber 11 may be given moderate elasticity, and thus moderate followability along the blood vessel V. Therefore, it is possible to acquire such an effect that the sensor part 11a is easily inserted into the blood vessel V and also easily removed from the blood vessel V. The tubular member 14 is made of a metallic material or a synthetic resin material, for example. The tubular member 14 is also an example of a support member that exhibits flexibility and supports the optical fiber 11.

With the present embodiment, it is also possible to acquire the effects similar to those of the first embodiment described above. The pressure measurement device 10C of the present embodiment may be applied to an invasive blood pressure measurement device that directly measures the pressure of an in vivo fluid by the sensor part 11a located inside a living body.

Figure 8:
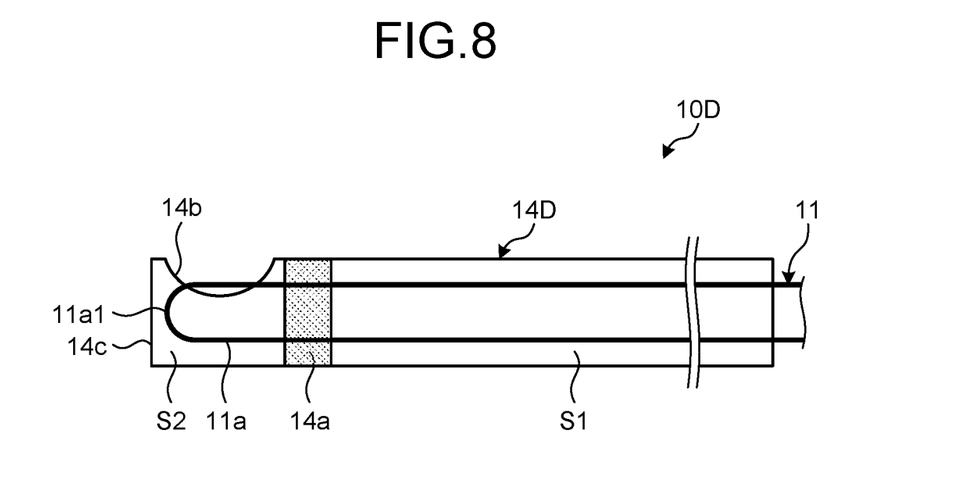
FIG. 8 is an exemplary schematic diagram of an in vivo pressure measurement device according to a modification of the third embodiment.

FIG. 8 is a schematic diagram of a part of a pressure measurement device 10D according to a modification of the third embodiment, which is a cross-sectional view along the longitudinal direction of an optical fiber 11 in a blood vessel V. The optical fiber 11 of the present modification is optically connected to a light source 21 and a light receiving unit 22, as in the first embodiment described above. In other words, in the present modification, test light input into the optical fiber 11 from the light source 21 is also transmitted in the optical fiber 11 including a sensor part 11a, and received at the light receiving unit 22. A control unit 30 calculates the pressure acted on the sensor part 11a based on the optical intensity of the test light received at the light receiving unit 22. Furthermore, the sensor part 11a of the present modification is inserted into a blood vessel V, as in the third embodiment described above.

As illustrated in FIG. 8, in the present modification, a cover 14c that is a tip part (one part) of a tubular member 14D covers the sensor part 11a. Note, however, that an opening 14b is provided in the peripheral wall (sidewall) of the cover 14c. Thereby, the sensor part 11a comes in contact with the blood F1 that is introduced into the cover 14c from the blood vessel V via the opening 14b. In other words, the sensor part 11a is located in the blood. Furthermore, a fixing member 14a sections the inside of the tube of the tubular member 14 into a space S1 and a space S2 that is opened by the opening 14b. At least a part of the sensor part 11a is disposed in the space S2. With such a configuration, the sensor part 11a along with the optical fiber 11 may be protected by the tubular member 14D. Note that the cover 14c may be configured with a member that is different from the tubular member 14 and attached to the tubular member 14.

The pressure measurement device 10D of the present modification may be applied to an invasive blood pressure measurement device that directly measures the pressure of an in vivo fluid by the sensor part 11a located inside a living body.

Figure 9:
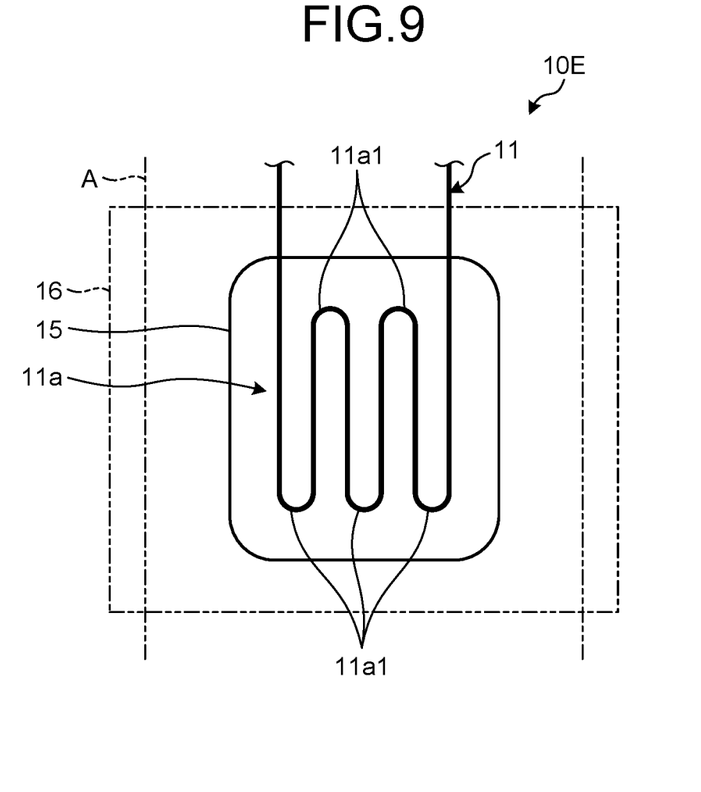
FIG. 9 is an exemplary schematic diagram of an in vivo pressure measurement device according to a fourth embodiment.

FIG. 9 is a schematic diagram of a pressure measurement device 10E according to a fourth embodiment, which is a plan view illustrating a state being attached outside a living body A. An optical fiber 11 of the present embodiment is optically connected to a light source 21 and a light receiving unit 22, as in the first embodiment described above. In other words, in the present embodiment, test light input into the optical fiber 11 from the light source 21 is also transmitted in the optical fiber 11 including a sensor part 11a, and received at the light receiving unit 22. A control unit 30 calculates the pressure acted on the sensor part 11a based on the optical intensity of the test light received at the light receiving unit 22.

As illustrated in FIG. 9, in the present embodiment, the sensor part 11a is disposed, together with a pad 15 and a cuff 16, on the outer skin of the living body A, such as an arm, for example.

The pad 15 exhibits flexibility and has a sheet-like shape. The pad 15 is placed on the outer skin of the living body A while being in contact therewith. The sensor part 11a (optical fiber 11) is disposed on the opposite side of the outer skin of the living body A with respect to the pad 15. In other words, the pad 15 is interposed between the sensor part 11a and the outer skin of the living body A. The sensor part 11a is fixed to the pad 15 by, for example, an adhesive or the like.

The cuff 16 is wrapped around the living body A, for example, around the arm, so as to cover the pad 15 and the sensor part 11a.

Furthermore, the sensor part 11a is bent a plurality of times via a plurality of curved parts 11a1. Such a configuration may expand the area where sensing is possible.

Figure 10:
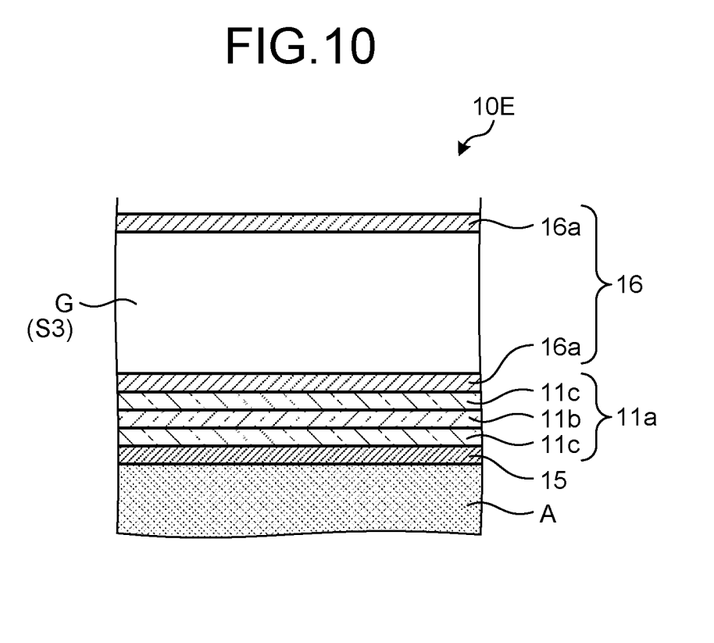
FIG. 10 is an exemplary and schematic diagram of a part of the in vivo pressure measurement device according to the fourth embodiment.

FIG. 10 is a cross-sectional view of the pressure measurement device 10E perpendicular to the pad 15. As illustrated in FIG. 10, the pad 15, the sensor part 11a, and the cuff 16 are stacked in this order on the outer skin of the living body A. The sensor part 11a is disposed between the pad 15 and the cuff 16. The pad 15, the sensor part 11a, and the cuff 16 may or may not be fixed to each other by an adhesive or the like.

The cuff 16 has a space S3 capable of housing gas G such as air, for example, provided between a sheet 16a close to the living body A and a sheet 16a far from the living body A. The space S3 is connected to an electric pump and an electric valve, not illustrated. The cuff 16 is configured such that the pressure of the gas G in the space S3 may be changed by controlling the electric pump and the electric valve. Specifically, the cuff 16 is configured to allow the pressure of the gas G in the space S3 to increase and then to decrease gradually over time, for example. With such a configuration, the control unit 30 may acquire the maximum blood pressure and the minimum blood pressure by well-known oscillometric methods in blood pressure monitors using the cuff 16, for example, based on the detection values of the sensor part 11a or the changes over time of the blood pressure pulsation acquired from the detection values.

With the present embodiment, it is also possible to acquire the effects similar to those of the first embodiment described above. The pressure measurement device 10E of the present embodiment may be applied to a non-invasive blood pressure measurement device that indirectly measures the pressure of an in vivo fluid via the living body A by the sensor part 11a located outside the living body.

Figure 11:
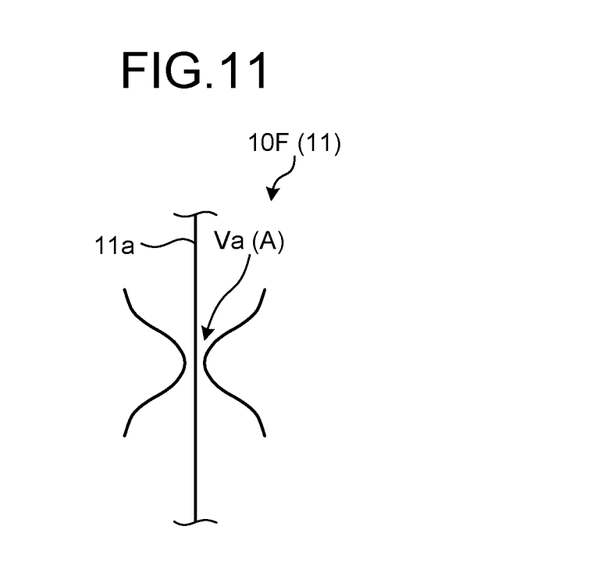
FIG. 11 is an exemplary schematic diagram of an in vivo pressure measurement device according to a fifth embodiment, which illustrates a state where no pressure is acting on the sensor part from a living body.
Figure 12:
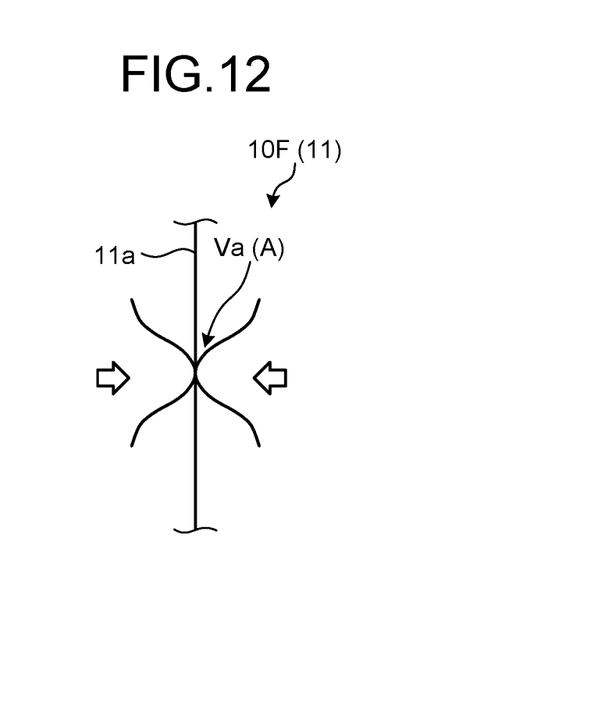
FIG. 12 is an exemplary schematic diagram of the in vivo pressure measurement device according to the fifth embodiment, which illustrates a state where pressure is acting on the sensor part from the living body.

FIGS. 11 and 12 are schematic diagrams of a pressure measurement device 10F according to a fifth embodiment. The pressure measurement device 10F measures not the pressure of a fluid in the living body A but the pressure acting on a sensor part 11a of an optical fiber 11 from a valve part Va of the living body A, that is, the pressure received from a body part in the living body. The valve part Va has a constriction part (throat), and the sensor part 11a penetrates through the constriction. The valve part Va is, for example, the heart valve, the pylorus of the stomach, or the like. FIG. 11 illustrates a state where the constriction part is widened relatively large, with no pressure acting on the sensor part 11a from the valve part Va, that is, from the living body A. On the other hand, FIG. 12 illustrates a state where the constriction part is narrowed relatively small, with pressure acting on the sensor part 11a from the valve part Va. In the state illustrated in FIG. 12, the outer periphery of the sensor part 11a is dented due to the force received from the valve part Va, thereby increasing leakage of the test light from the sensor part 11a and increasing the transmission loss for the test light at the sensor part 11a compared to the state illustrated in FIG. 11. Therefore, the control unit 30 may calculate the pressure acted on the sensor part 11a corresponding to the intensity of light received at the light receiving unit 22 based on a correlation between the intensity of the light received at the light receiving unit 22 acquired in advance experimentally and the pressure acted on the sensor part 11a from the valve part Va. Note that the pressure measurement device 10F may also measure the force (load) acted on the sensor part 11a from the valve part Va. In other words, in the present embodiment, the pressure measurement device 10F may also function as an in vivo force measurement device (load measurement device).

Figure 13:
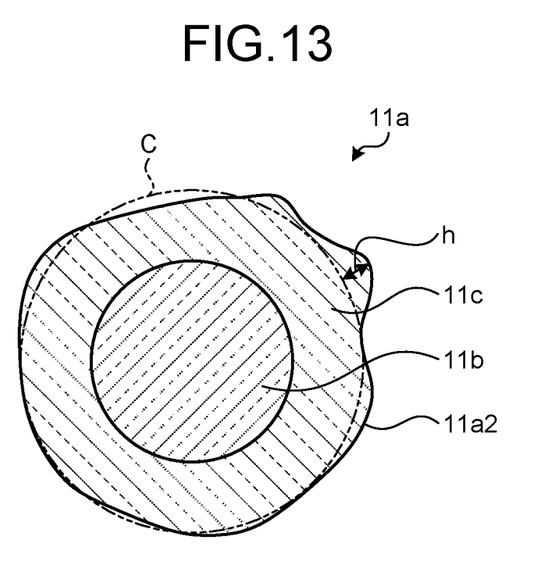
FIG. 13 is an exemplary and schematic cross-sectional view perpendicular to the longitudinal direction of the sensor part according to a modification of the embodiment.

FIG. 13 is a cross-sectional view perpendicular to the longitudinal direction of a sensor part 11a according to a modification of the embodiments. As illustrated in FIG. 13, an outer periphery 11a2 of the sensor part 11a, that is, an outer periphery 11a2 of a cladding 11c, may be provided with an uneven structure including concave or convex parts. The uneven structure may also be referred to as structural fluctuation. By setting the size of the uneven structure, such as the length of the uneven structure in the longitudinal direction, the spacing, and the height difference in the radial direction, for example, to appropriate values, the transmission loss for the test light at the sensor part 11a may be made to 0.3 dB/m or more. Through the intensive studies of the inventors, it is found that the size of the concave and convex of the uneven structure is preferable to be between 5 [nm] and 100 [nm], both inclusive. As an example of an index of the size of the uneven structure, FIG. 13 illustrates a deviation h of the average radius of the outer periphery 11a2 from a circumference C in the cross section perpendicular to the longitudinal direction of the sensor part 11a. The deviation h is also preferable to be between 5 [nm] and 100 [nm], both inclusive. Note that the uneven structure may be provided on the outer periphery of the core 11b. In addition, in the present modification, the sensor part 11a may also be made of plastic fibers, for example.

While the embodiments and modifications of the present disclosure are presented above, the embodiments and modifications are examples and are not intended to limit the scope of the present disclosure. The embodiments and modifications described above may be implemented in various other forms, and various omissions, substitutions, combinations, and changes are possible without departing from the gist of the present disclosure. In addition, each constituent element, shape, and other specifications (structure, type, direction, model, size, length, width, thickness, height, number, arrangement, position, material, and the like) may be changed as appropriate.

For example, the configurations of the embodiments and modifications described above may also be applied to measurement of pressure of in vivo fluids other than blood, measurement of pressure received from body parts in a living body other than the valve part such as the heart valve, the pylorus of the stomach, and the like.

Furthermore, the support member is not limited to the tubular member, but may be a rod-shaped member or the like that exhibits flexibility, for example. In that case, the optical fiber may extend linearly or spirally along the outer periphery of the support member. Furthermore, the optical fiber may be housed in a linear or helical groove provided on the outer periphery of the support member.

In addition, optical fibers with different mode transmission states from each other may be applied to the sensor part and the delivery optical fiber such that mode conversion occurs at the connection point (boundary) between the sensor part (sensor optical fiber) and the delivery optical fiber between the sensor part and the light source. In this case, mode conversion at the connection point depends on the external force, and the mode mismatch state also depends on the external force. Therefore, the degree of leakage of the test light at the sensor part becomes more sensitive to the external force, which results in increasing the sensitivity of the sensor part further to the pressure in the living body.

The present disclosure may be utilized for in vivo pressure measurement devices.

According to the present disclosure, for example, it is possible to acquire an improved and new in vivo pressure measurement device.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An in vivo pressure measurement device comprising:
a light source configured to output test light;
an optical fiber, to which the test light is input, at least partially including a sensor optical fiber configured to transmit the test light with a loss of 0.3 dB/m or more; and
a light receiving unit configured to receive the test light transmitted through the sensor optical fiber, wherein
the in vivo pressure measurement device is configured to measure pressure in a living body acting on the sensor optical fiber based on an intensity of the test light received at the light receiving unit, and
the sensor optical fiber includes a core, a cladding surrounding the core, and a plurality of nanostructures near an interface between the core and the cladding.

2. The in vivo pressure measurement device according to claim 1, wherein the pressure in the living body is pressure of a fluid in the living body.

3. The in vivo pressure measurement device according to claim 1, wherein the sensor optical fiber is a plastic fiber.

4. The in vivo pressure measurement device according to claim 1, wherein the sensor optical fiber includes a curved part.

5. The in vivo pressure measurement device according to claim 1, wherein the sensor optical fiber is configured to be inserted into the living body.

6. The in vivo pressure measurement device according to claim 1, wherein the sensor optical fiber is configured to measure pressure of an ex vivo fluid to which pressure of an in vivo fluid is propagated.

7. The in vivo pressure measurement device according to claim 1, comprising a flexible support member configured to extend along the optical fiber and support the optical fiber.

8. The in vivo pressure measurement device according to claim 1, comprising a tubular member configured to house the optical fiber.

9. The in vivo pressure measurement device according to claim 8, wherein the tubular member is flexible.

10. The in vivo pressure measurement device according to claim 1, comprising a cover configured to cover the sensor optical fiber in a state capable of introducing an in vivo fluid or an ex vivo fluid to which pressure of the in vivo fluid is propagated.

11. The in vivo pressure measurement device according to claim 1, wherein the sensor optical fiber is located outside the living body, and configured to measure pressure of an in vivo fluid indirectly acting on the sensor optical fiber via the living body.

12. The in vivo pressure measurement device according to claim 11, wherein the sensor optical fiber is configured to be disposed between the living body and a cuff located outside the living body, the cuff being configured to constrict a blood vessel in the living body by internal air pressure and change the internal air pressure.

13. The in vivo pressure measurement device according to claim 1, wherein the optical fiber includes:
the sensor optical fiber; and
a delivery optical fiber connected to the sensor optical fiber and having a lower transmission loss than the sensor optical fiber does.

14. The in vivo pressure measurement device according to claim 13, wherein, in wavelengths of the test light,
the sensor optical fiber is a single-mode optical fiber, and
the delivery optical fiber between the sensor optical fiber and the light source is a multi-mode optical fiber.

15. The in vivo pressure measurement device according to claim 13, wherein the sensor optical fiber and the delivery optical fiber are fusion-spliced.

16. The in vivo pressure measurement device according to claim 1, wherein the light receiving unit is configured to receive the test light input from one end of the optical fiber and output from another end of the optical fiber.

17. The in vivo pressure measurement device according to claim 1, wherein
each nanostructure of the plurality of nanostructures has a cross-sectional diameter of 100 nm or less in a cross section perpendicular to a longitudinal direction of the sensor optical fiber.

18. The in vivo pressure measurement device according to claim 17, wherein each nanostructure of the plurality of nanostructures is a microparticle, a tube or a void.

19. The in vivo pressure measurement device according to claim 1, wherein an outer periphery of the sensor optical fiber includes an uneven structure of 5 nm to 100 nm.

20. The in vivo pressure measurement device according to claim 1, comprising an arithmetic processing unit configured to acquire the pressure acting on the sensor optical fiber based on the intensity of the test light.

21. An in vivo pressure measurement device comprising:
a light source configured to output test light;
an optical fiber, to which the test light is input, including a sensor part from which light leaks due to an applied external force; and
a light receiving unit configured to receive the test light transmitted through the sensor part, wherein
the in vivo pressure measurement device is configured to measure pressure in a living body acting on the sensor part based on intensity of the test light received at the light receiving unit, and
the sensor part includes a core, a cladding surrounding the core, and a plurality of nanostructures near an interface between the core and the cladding.

22. The in vivo pressure measurement device according to claim 21, wherein a transmission loss in the sensor part increases as the external force acting on the sensor part increases.

* * * * *